(12) United States Patent
Satoh

(10) Patent No.: US 7,207,940 B2
(45) Date of Patent: Apr. 24, 2007

(54) ULTRASONIC PROBE AND ULTRASONIC TRANSMITTING AND RECEIVING APPARATUS USING THE SAME

(75) Inventor: Tomoo Satoh, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/670,601

(22) Filed: Sep. 26, 2003

(65) Prior Publication Data
US 2004/0220463 A1 Nov. 4, 2004

(30) Foreign Application Priority Data
Sep. 30, 2002 (JP) ............................. 2002-285948
Aug. 19, 2003 (JP) ............................. 2003-207853

(51) Int. Cl.
*A61B 8/00* (2006.01)

(52) U.S. Cl. .................................................. 600/437

(58) Field of Classification Search ................ 600/437, 600/443, 447, 456, 458; 73/625–626; 128/916
See application file for complete search history.

(56) References Cited

U.S. PATENT DOCUMENTS

| | | | | |
|---|---|---|---|---|
| 4,545,251 A | * | 10/1985 | Uchida et al. ................ 73/631 |
| 4,811,740 A | * | 3/1989 | Ikeda et al. .................. 600/437 |
| 4,893,284 A | * | 1/1990 | Magrane ....................... 367/12 |
| 5,092,336 A | * | 3/1992 | Fink ............................. 600/443 |
| 5,092,337 A | * | 3/1992 | Uchiumi et al. ............. 600/447 |
| 5,209,235 A | * | 5/1993 | Brisken et al. .............. 600/466 |
| 5,251,631 A | * | 10/1993 | Tsuchiko et al. ........... 600/447 |
| 5,517,994 A | * | 5/1996 | Burke et al. ................. 600/437 |
| 5,520,187 A | * | 5/1996 | Snyder ......................... 600/459 |
| 5,544,660 A | * | 8/1996 | Crowley ....................... 600/466 |
| 5,657,761 A | * | 8/1997 | Okada et al. ............... 600/437 |
| 5,676,149 A | * | 10/1997 | Yao ............................. 600/437 |
| 5,808,962 A | * | 9/1998 | Steinberg et al. ............ 367/7 |
| 5,891,041 A | * | 4/1999 | Shinomura et al. ......... 600/459 |
| 5,893,832 A | * | 4/1999 | Song ............................ 600/443 |
| 6,053,871 A | * | 4/2000 | Cockburn .................... 600/459 |
| 6,120,449 A | * | 9/2000 | Snyder et al. .............. 600/447 |
| 6,279,399 B1 | * | 8/2001 | Holm ........................... 73/626 |
| 6,364,839 B1 | * | 4/2002 | Little et al. ................. 600/459 |
| 6,500,126 B1 | * | 12/2002 | Brock-Fisher ............. 600/459 |

(Continued)

OTHER PUBLICATIONS

Richard E. Davidsen, et al. "Two-Dimensional Arrays for Medical Ultrasound Using Multilayer Flexible Circuit Interconnections" IEEE Transactions on Ultrasonics, Ferroelectrics and Frequency Control, vol. 45, No. 2, Mar. 1998, pp. 338-348.

(Continued)

*Primary Examiner*—Francis J. Jaworski
(74) *Attorney, Agent, or Firm*—Sughrue Mion, PLLC

(57) ABSTRACT

An ultrasonic probe in which transducer array including ultrasonic transducers out of the specifications can be used so that the yield in the manufacture of transducer arrays is improved. The ultrasonic probe to be used when connected to an external apparatus main body includes: a transducer array including plural ultrasonic transducers; a connecting portion for connecting ultrasonic transducers selected from among the plural ultrasonic transducers to the external apparatus main body; and an identification information holding portion for holding identification information on the ultrasonic probe which information is associated with arrangement information and/or characteristic information on the selected ultrasonic transducers within the transducer array.

8 Claims, 14 Drawing Sheets

U.S. PATENT DOCUMENTS

| | | | | |
|---|---|---|---|---|
| 6,503,204 B1 | * | 1/2003 | Sumanaweera et al. | 600/459 |
| 6,552,964 B2 | * | 4/2003 | Chiang et al. | 367/138 |
| 6,565,510 B1 | * | 5/2003 | Haider | 600/437 |
| 6,656,119 B2 | * | 12/2003 | Sasaki et al. | 600/437 |
| 6,783,497 B2 | * | 8/2004 | Grenon et al. | 600/459 |

OTHER PUBLICATIONS

Richard E. Davidsen, et al., "Two-Dimensional Random Arrays for Real Time Volumetric Imaging" Ultrassonic Imaging 16, pp. 143-163 (1994).

* cited by examiner

ARRANGEMENT PATTERN OF ELEMENTS FOR TRANSMISSION

ARRANGEMENT PATTERN OF ELEMENTS FOR RECEPTION

ARRANGEMENT PATTERN OF ELEMENTS FOR TRANSMISSION/RECEPTION

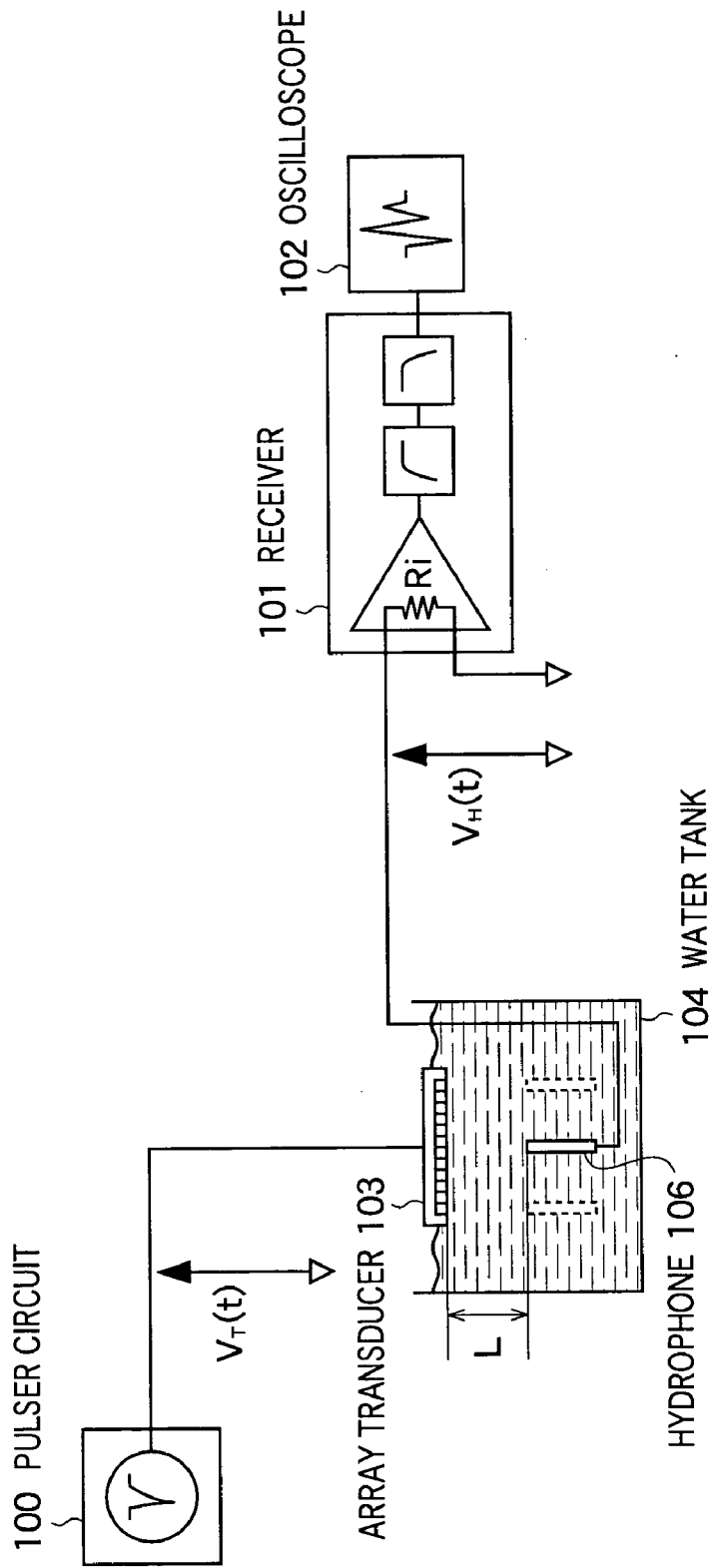

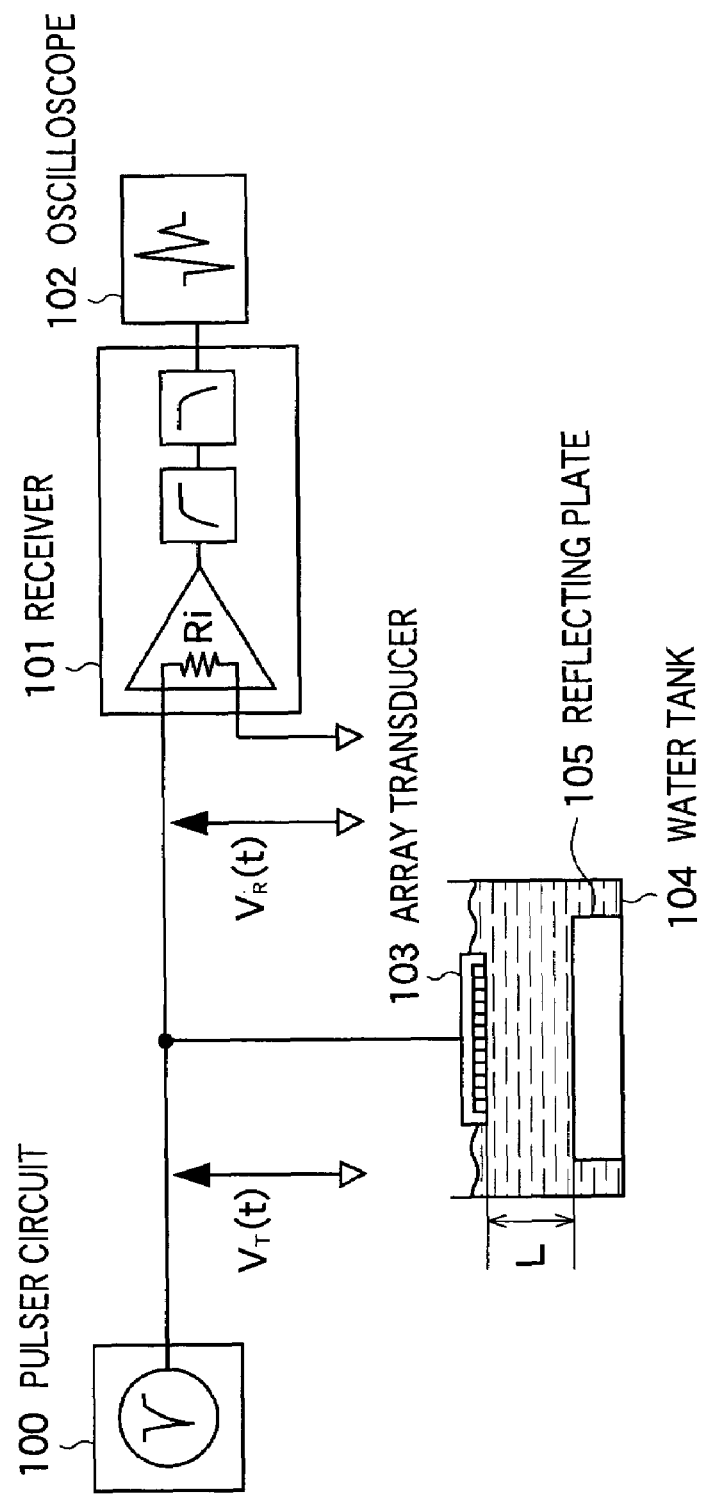

ULTRASONIC PROBE AND ULTRASONIC TRANSMITTING AND RECEIVING APPARATUS USING THE SAME

BACKGROUND OF THE INVENTION

1. Field of the Invention

The present invention relates to an ultrasonic probe and an ultrasonic transmitting and receiving apparatus to be used for observing internal organs in a living body, etc. by transmitting and receiving ultrasonic waves.

2. Description of a Related Art

Conventionally, in order to acquire a three-dimensional image by transmitting and receiving ultrasonic waves, two-dimensional images with regard to cross sections in a depth direction are acquired by using a one-dimensional sensor array having a position sensor to electrically steer the received ultrasonic waves, and further, a three-dimensional image is constructed by combining the plural two-dimensional images acquired by mechanically moving this one-dimensional sensor. However, by this technique, since there is a time lag in the mechanical movement of the one-dimensional array, the plural two-dimensional images at different times are combined and the composite image results in a blurred image. Therefore, this technique is unsuitable for imaging of an object accompanied by motion, such as a living organism.

In order to overcome such defects, it is more advantageous that a three-dimensional image is acquired by using a two-dimensional sensor array. However, since the number of ultrasonic detecting elements included in the two-dimensional sensor array becomes exceedingly larger than that in the one-dimensional array, new problems will arise. For example, when using a two-dimensional sensor array having an order of 80×80 elements, it is ideal that all of the elements are used for receiving ultrasonic waves. However, a problem such that wiring becomes more complicated with the larger number of elements arises in the manufacture of the two-dimensional sensor array. In addition, since there is a requirement for as many channels in the electrical circuit for processing the detection signals, which are obtained by detecting ultrasonic waves by using the ultrasonic detecting elements, as there are ultrasonic detecting elements, the electrical circuit becomes unduly complicated.

Under the circumstances, in order to reduce the number of channels of the electrical circuit for processing the detection signals, a "sparse array" approach is used. In such approach, only a part of the ultrasonic elements, which are included in the plural ultrasonic detecting elements arranged in a two-dimensional manner, are used.

For example, a sparse array, in which 40×40 ultrasonic transducers are provided inside of an aperture of an ultrasonic probe and about 30% of the ultrasonic transducers are used, is disclosed in Richard E. Davidsen et al. "TWO-DIMENSIONAL ARRAYS FOR MEDICAL ULTRASOUND USING MULTILAYER FLEXIBLE CIRCUIT INTERCONNECTION", IEEE TRANSACTIONS ON ULTRASONICS, FERROELECTRICS, AND FREQUENCY CONTROL, VOL. 45, NO. 2, 1998 March, pp. 338–348.

Further, an arrangement of a sparse array, which is considered so that a high-quality sound field may be obtained by reducing side lobes, is disclosed in Richard E. Davidsen et al. "TWO-DIMENSIONAL RANDOM ARRAYS FOR REAL TIME VOLUMETRIC IMAGING", ULTRASONIC IMAGING 16 (1994), Academic Press Inc., pp. 143–163.

Moreover, in the case where a transducer array having plural ultrasonic transducers is manufactured, the respective ultrasonic transducers are subjected to an inspection as to whether or not they operate with a predetermined performance. If there is only one transducer out of the specifications, that entire transducer array is treated as a defective product. For the two-dimensional transducer array, where the number of ultrasonic transducers is large and the size is smaller than those in the one-dimensional transducer array, the rate of occurrence of defective products is increased.

In the case where an ultrasonic probe is manufactured by using the above described sparse array approaches, the number of ultrasonic transducers to be used is smaller than in the case where all of the transducers inside of the aperture of the ultrasonic probe, are used. Therefore, the rate of occurrence of a defective products can becomes lower due to the smaller number. However, even if there is only one ultrasonic transducer that is out of the specifications among all of the ultrasonic transducers that are to be used in accordance with the design of the sparse array, the transducer array is still treated as a defective product. Thus the yield in the manufacture of transducer arrays continue to be low.

SUMMARY OF THE INVENTION

The present invention has been achieved by considering the above-described circumstances. A first object of the present invention is to provide an ultrasonic probe in which a transducer array, even one including ultrasonic transducers that are out of an original specification, can be used in a range where image quality is unaffected, and by which the yield in the manufacture of transducer arrays can be improved. Further, a second object of the present invention is to provide an ultrasonic transmitting and receiving apparatus using such an ultrasonic probe.

In order to solve the above described problems, an ultrasonic probe D according to one aspect of the present invention B is an ultrasonic probe to be used when connected to an external apparatus main body, and comprises: a transducer array including plural ultrasonic transducers; connecting means used for connecting ultrasonic transducers selected from among the plural ultrasonic transducers to the external apparatus main body; and identification information holding means for holding identification information on the ultrasonic probe which information is associated with arrangement information and/or characteristic information on the selected ultrasonic transducers within the transducer array. ultrasonic probe which information is associated with arrangement information and/or characteristic information on the selected ultrasonic transducers within the transducer array.

Further, an ultrasonic transmitting and receiving apparatus according to one aspect of the present invention is an ultrasonic transmitting and receiving apparatus to be used when connected to an ultrasonic probe including a transducer array including plural ultrasonic transducers, connecting means for connecting ultrasonic transducers selected from among the plural ultrasonic transducers to an ultrasonic transmitting and receiving apparatus main body, and identification information holding means for holding identification information, and comprises: plural transmitting circuits for respectively generating and plural driving signals to be supplied to the ultrasonic probe so as to transmit an ultrasonic beam; plural receiving circuits for respectively processing plural detection signals outputted from the ultrasonic probe which has received an ultrasonic echo; and control means for controlling delay amounts of the plural driving signals in the plural transmitting circuits and/or delay amounts of the plural detection signals in the plural receiving circuits in correspondence with the ultrasonic probe identified on the basis of the identification information.

According to the present invention, by selecting the ultrasonic transducers to be used while avoiding ultrasonic transducers out of the specifications, the arrangement of the ultrasonic transducers to be used in one transducer array is determined. Further, the arrangement information and/or characteristic information on the ultrasonic transducers to be used have been recorded in correspondence with identification information on that ultrasonic probe, and the information is utilized in the ultrasonic transmitting and receiving apparatus main body. Therefore, a transducer array, which has been unable to be used because it includes ultrasonic transducers out of the specifications, can be used, and the yield in the manufacture of transducer arrays can be improved. In this application, a transducer as an element included in a transducer array is referred to as "an ultrasonic transducer".

BRIEF DESCRIPTION OF THE DRAWINGS

FIG. 4 is a schematic diagram showing first inspection equipment used for inspecting transmission characteristics of an array transducer;

FIG. 5 is a schematic diagram showing second inspection equipment used for inspecting reception characteristics of the array transducer;

DESCRIPTION OF THE PREFERRED EMBODIMENTS

Figure 1:
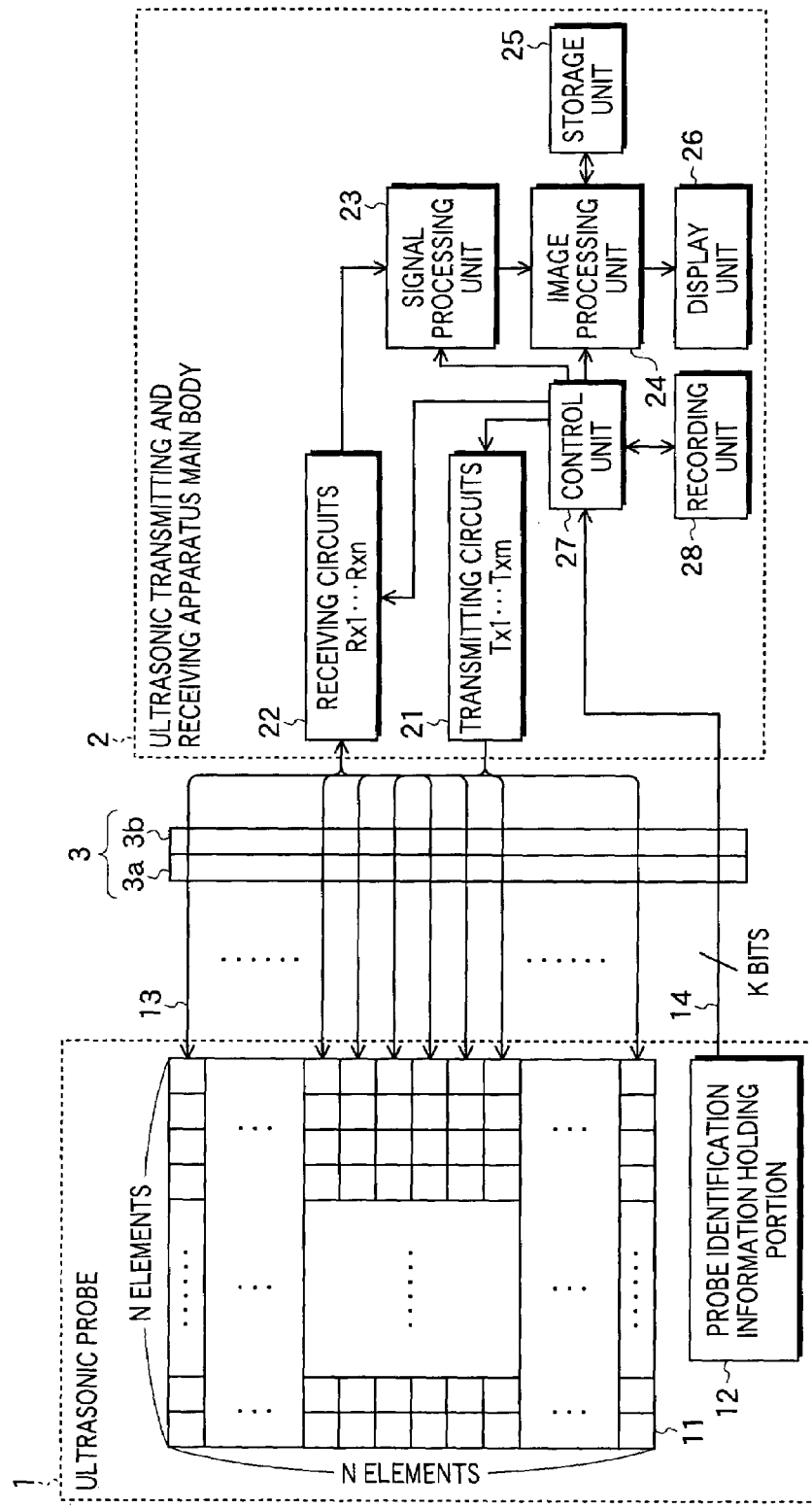
FIG. 1 is a block diagram showing a constitution of an ultrasonic transmitting and receiving apparatus according to one embodiment of the present invention.

Now, referring to the drawings, an embodiment of the present invention will be described.

FIG. 1 is a block diagram showing a constitution of an ultrasonic transmitting and receiving apparatus according to one embodiment of the present invention. As shown in FIG. 1, this ultrasonic transmitting and receiving apparatus includes an ultrasonic probe 1 to be used in contact with an object to be inspected, an ultrasonic transmitting and receiving apparatus main body 2 connected to the ultrasonic probe 1, and a connector 3 for connecting therebetween. The connector 3 is constituted by a primary side connector 3a to which wiring of the ultrasonic probe 1 is connected and a secondary side connector 3b to which wiring of the ultrasonic transmitting and receiving apparatus main body 2 is connected. By the way, the primary side connector 3a may be fixed to the ultrasonic probe 1, or the secondary side connector 3b may be fixed to the ultrasonic transmitting and receiving apparatus main body 2.

The ultrasonic probe 1 has a transducer array (hereinafter, also referred as "array transducer") 11 that includes $N^2$ ultrasonic transducers arranged in a two-dimensional matrix form, and a probe identification information holding portion 12. From among $N^2$ ultrasonic transducers, m of them are used for ultrasonic transmission, and n of them are used for ultrasonic reception, where m, $n<N^2$. These ultrasonic transducers are connected to the ultrasonic transmitting and receiving apparatus main body 2 via signal lines 13 and the connector 3.

As the ultrasonic transducer, for example, a piezoelectric ceramic represented by PZT (Pb (lead) zirconate titanate) or a macromolecule piezoelectric element such as PVDF (polyvinylidene difluoride) is used. In addition, a piezoelectric element including PZNT (oxide including lead, zinc, niobium, and titanium) monocrystal that is recently expected to contribute to improvements in sensitivity and bandwidth of an ultrasonic transducer may be used.

The probe identification information holding portion 12 holds probe identification information such as serial numbers, etc. to be used for identifying individual ultrasonic probes. This probe identification information is associated with arrangement information and/or characteristic information on ultrasonic transducers to be used actually in the plural ultrasonic transducers included in the array transducer 11. In the probe identification information holding portion 12, for example, by making each of K probe identification lines 14 to connect to ground potential or to be open, K-bit probe identification information can be held. By the way, without using such electrical probe identification information holding portion 12, serial numbers, etc. may be simply displayed on the ultrasonic probe 1 so that an operator identifies the individual probes to operate the ultrasonic transmitting and receiving apparatus main body 2.

Figure 2:
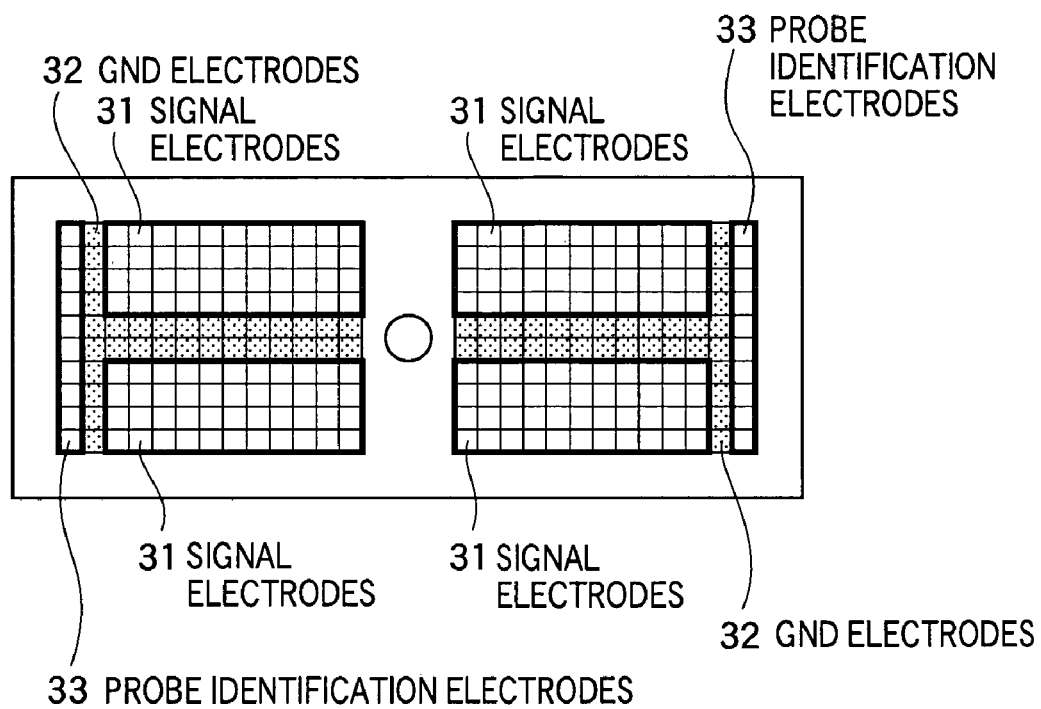
FIG. 2 is a diagram showing an arrangement of electrodes in a connector shown in FIG. 1.

In the connector 3a or 3b, the electrodes that have been conventionally unused are used for probe identification. Specifically, as shown in FIG. 2, probe identification electrodes 33 are provided for connecting K probe identification lines 14 to the ultrasonic transmitting and receiving apparatus main body 2, other than the signal (hot side) electrodes 31 and GND (cold side) electrodes 32. In the connector shown in FIG. 2, 2×10 electrodes (pins) on both sides are used for probe identification. For example, depending on whether the respective pins are made to connect to ground potential or to be open, a binary value is assigned to each of the respective 20 pins. Thereby, $(2^{20}-1)$ different probes can be identified.

Referring to FIG. 1 again, the ultrasonic transmitting and receiving apparatus main body 2 includes plural transmitting circuits 21, plural receiving circuits 22, a signal processing unit 23, an image processing unit 24, a storage unit 25, a display unit 26, a control unit 27, and a recording unit 28. The control unit 27 identifies individual ultrasonic probes on the basis of the K-bit probe identification information, reads out from the recording unit 28 a delay amount table that corresponds to the arrangement of the ultrasonic transducers to be used in that ultrasonic probe, and controls delay amounts of the respective channels in the plural transmitting circuits 21 and the plural receiving circuits 22 based thereon. In the recording unit 28, a recording medium such as a hard disk, flexible disk, MO, MT, RAM, CD-ROM, or DVD-ROM can be used. It is conceivable that a delay amount table corresponding to one ultrasonic probe is recorded on one flexible disk, and supplied to a user with the ultrasonic probe. Alternatively, the ultrasonic transmitting and receiving apparatus main body 2 may be connected to communicating means such as a network to receive data regarding a delay amount table corresponding to an ultrasonic probe via this network, etc.

The plural transmitting circuits 21 generates plural driving signals having delay amounts that correspond to the arrangement, etc. of the ultrasonic transducers to be used in that ultrasonic probe, respectively, and supplies them to the ultrasonic probe 1. Thereby, transmission beam forming is performed, and the ultrasonic probe 1 transmits an ultrasonic beam in a desired direction. The plural receiving circuits 22 perform processing such as amplification and delaying on plural detection signals outputted from the ultrasonic probe 1 which has received an ultrasonic echo, respectively. There are transmitting circuits 21 for m channels from Tx1 to Txm, and there are receiving circuits 22 for n channels from Rx1 to Rxn.

The signal processing unit 23 adds the detection signals that have been subjected to delaying processing and outputted from the plural receiving circuits 22. Thereby, reception beam forming is performed. The signal processing unit 23 also generates image data on the basis of the added detection signals. The image processing unit 24 performs image processing while once storing the image data outputted from the signal processing unit 23 into the storage unit 25. An ultrasonic image is displayed on the display unit 26 on the basis of the image signals outputted from the image processing unit 24.

Next, the arrangement of the ultrasonic transducers by which the present invention is characterized will be described. The present invention is mainly characterized by that, in a two-dimensional array transducer, in place of an ultrasonic transducer that has been judged as being defective, another transducer can be used. On the assumption of the concept of the present invention, the arrangement patterns of the ultrasonic transducers for transmission and reception shown in FIGS. 3A to 3C will be described as examples. In these examples, for simplicity, all of the numbers of the ultrasonic transducers (elements) are assumed as 41×41.

Figure 3A:
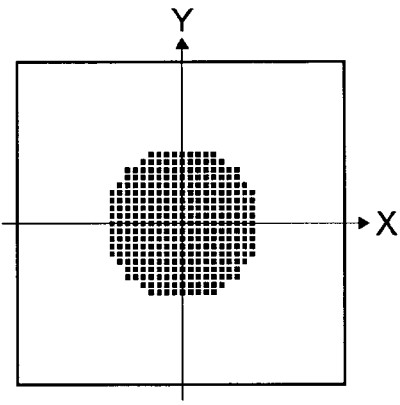
FIG. 3A to 3C are schematic diagrams showing examples of arrangement patterns of ultrasonic transducers for transmission and reception.

For transmission, all elements within a substantially circular form having a diameter equal to 17 elements, with a center of the array transducer as a center, are used. In this case, the number of elements for transmission is 226. The arrangement pattern of thus arranged ultrasonic transducers for transmission is shown in FIG. 3A.

On the other hand, the arrangement pattern of the ultrasonic transducers for reception is determined so as to satisfy the following conditions (1) to (3).
(1) The numbers of elements that exist in four quadrants, which are formed by dividing the array transducer by two axes (X axis and Y axis) orthogonal to each other, are balanced.
(2) In the case where the reception area is divided by drawing plural concentric circles from the center of the array transducer, the number of the elements that exist in the reception area divided by the adjacent two concentric circles is proportional to the dimensions of the area.
(3) The elements are arranged according to random numbers while satisfying the above conditions (1) and (2).

Figure 3B:
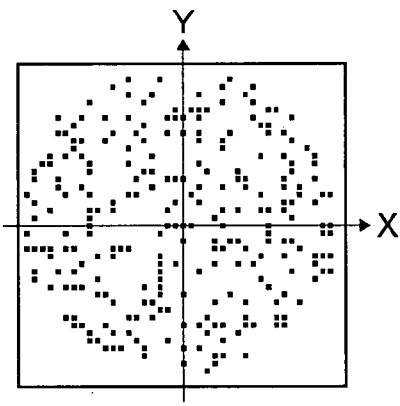
Figure 3C:
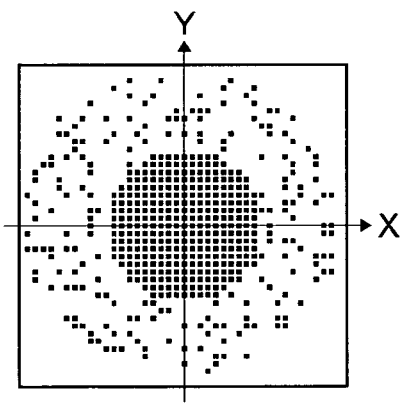

The arrangement pattern of thus arranged ultrasonic transducers for reception is shown in FIG. 3B. In addition, the pattern of the ultrasonic transducers for transmission or reception obtained by combining FIGS. 3A and 3B is shown in FIG. 3C.

When manufacturing the array transducer to be used for the ultrasonic probe in the embodiment, the inspection for measuring transmission characteristics and reception characteristics is preferably performed in regard to all of the ultrasonic transducers.

FIG. 4 is a schematic diagram showing first inspection equipment used for inspecting transmission characteristics of the manufactured array transducer. This inspection equipment includes a pulser circuit 100 for supplying pulsed driving signals to the ultrasonic transducers included in the array transducer 103 as an object of the inspection, a hydrophone 106 for detecting ultrasonic signals transmitted from the ultrasonic transducers, a receiver 101 for amplifying the detection signals outputted from the hydrophone 106 and performing filtering, and an oscilloscope 102 for observing the waveforms of the detection signals outputted from the receiver 101. The inspection equipment measures the characteristics of the ultrasonic transducer, according to which an electrical signal is converted into an ultrasonic signal.

The array transducer 103 is immersed into the water tank 104 filled with water, and the array transducer 103 and an upper surface of the hydrophone 106 are separated at a predetermined distance L. The driving signal is supplied to one of the transducers included in the array transducer 103 from the pulser circuit 100 to allow this ultrasonic transducer to transmit ultrasonic waves. The hydrophone 106 is guided right below this ultrasonic transducer, and the detection signal outputted from the hydrophone 106 that has received the ultrasonic waves is amplified by the receiver 101. The oscilloscope 102 records a waveform $V_T(t)$ of the driving signal and a waveform $V_R(t)$ of the detection signal.

By adjusting waveforms and amplitudes of the driving signal while monitoring the waveform of the detection signal so that uniform transmission waveforms are obtained as to all of the ultrasonic transducers to be used.

FIG. 5 is a schematic diagram showing second inspection equipment used for inspecting reception characteristics of the manufactured array transducer. This inspection equipment includes a pulser circuit 100 for supplying pulsed driving signals to the ultrasonic transducers included in the array transducer 103 as an object of the inspection, a receiver 101 for amplifying the detection signals outputted from the hydrophone 106 and performing filtering, and an oscilloscope 102 for observing the waveform of the detection signal outputted from the receiver 101. The inspection equipment measures the characteristics of the ultrasonic transducer, according to which an ultrasonic signal is converted in to an electrical signal. In regard to the elements in common with the first inspection equipment, they can be commonly used.

The array transducer 103 is immersed into the water tank 104 filled with water, and the array transducer 103 and an upper surface of a reflecting plate 105 are separated at a predetermined distance L. The metal reflecting plate 105 is placed at the bottom of the water tank 104. The driving signal is supplied to one of the transducers included in the array transducer 103 from the pulser circuit 100 to allow this ultrasonic transducer to transmit ultrasonic waves. The ultrasonic echo is generated by the transmitted ultrasonic waves being reflected on the upper surface of the reflecting plate 105, and the detection signal outputted from the ultrasonic transducer that has received the ultrasonic echo is amplified by the receiver 110. The oscilloscope 102 records a waveform $V_T(t)$ of the driving signal and a waveform $V_R(t)$ of the detection signal.

Next, after exchanging the ultrasonic transducer connected to the inspection equipment, the same inspection is performed on other ultrasonic transducers. The waveforms and amplitudes of the driving signals are adjusted so that uniform transmission waveforms are be obtained as to all of the used ultrasonic transducers on the basis of the measurement result obtained by using the first inspection equipment. As described above, all of the ultrasonic transducers within the array transducer are inspected.

Figure 6:
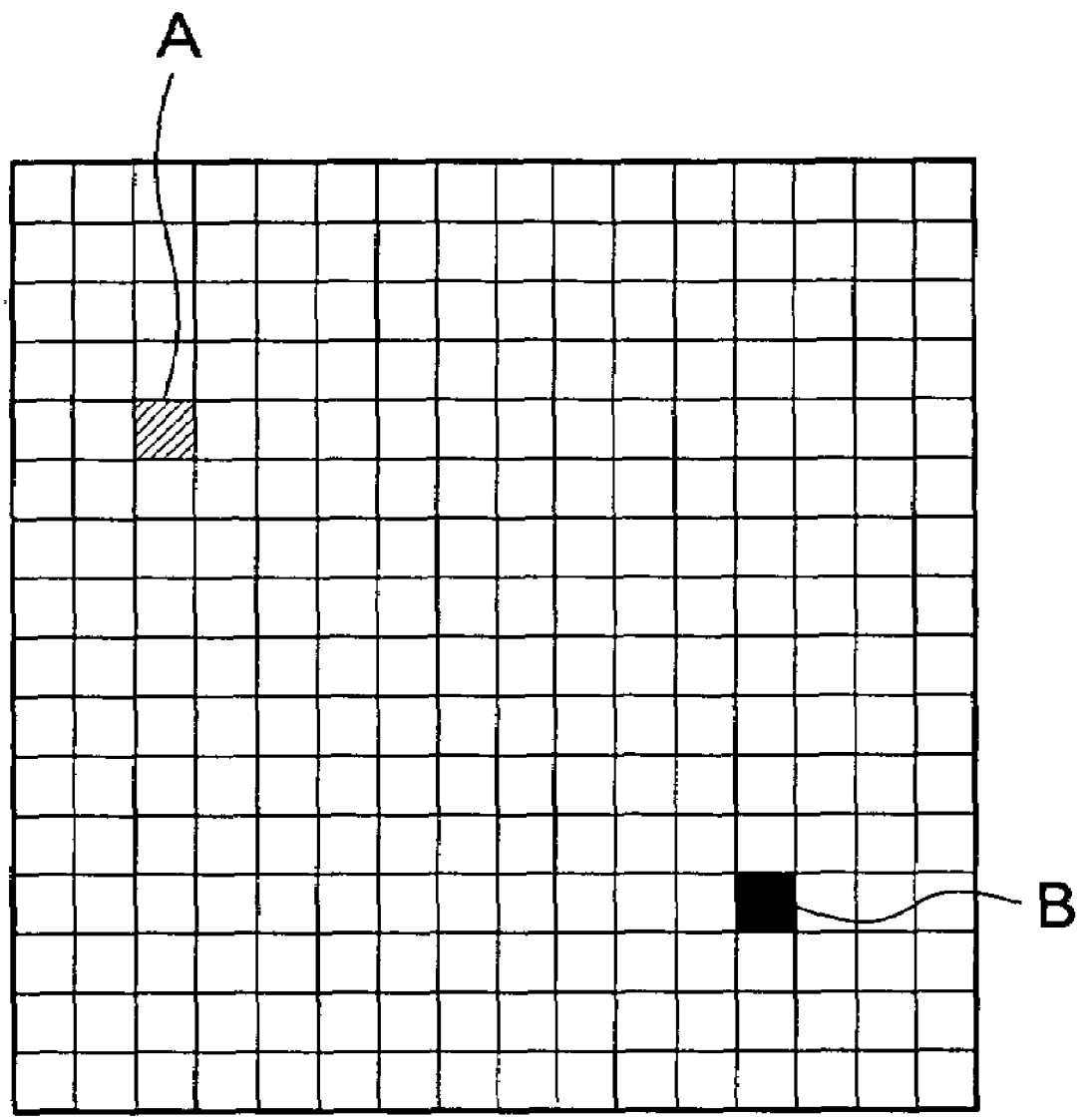
FIG. 6 is a diagram showing positions of two ultrasonic transducers in the array transducer.
Figure 7A:
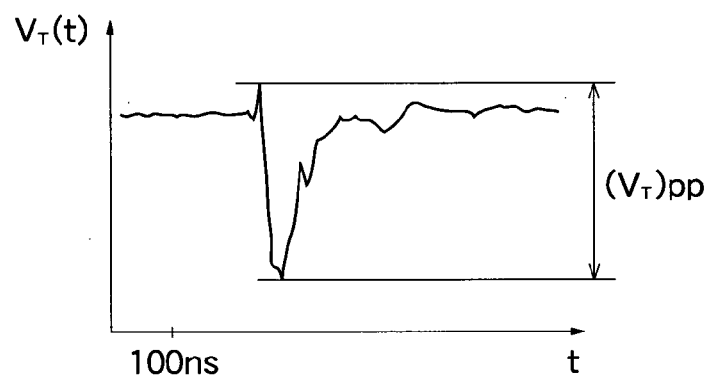
FIG. 7A to 7C are diagrams showing examples of waveforms that are recorded in the inspection of the array transducer.
Figure 7B:
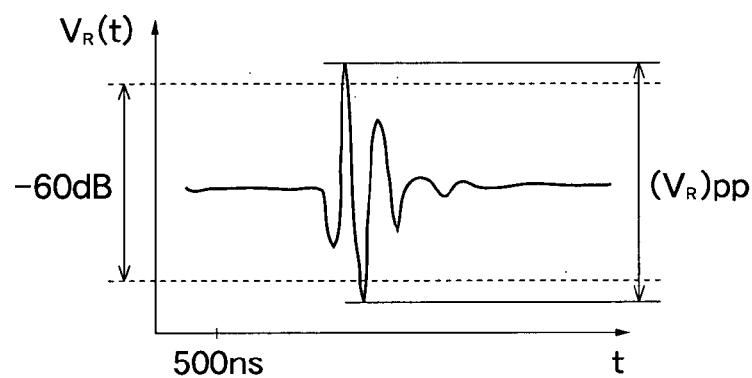
Figure 7C:
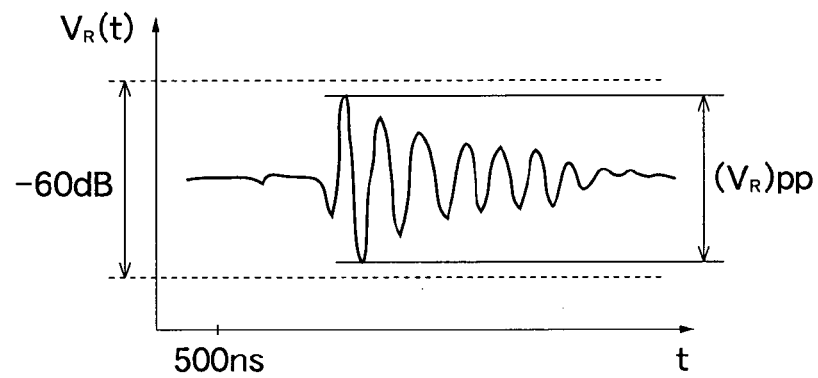

FIG. 6 shows positions of two ultrasonic transducers in the array transducer as an object of the inspection. Here, an ultrasonic transducer A and an ultrasonic transducer B are shown. FIGS. 7A to 7C show examples of waveforms recorded in the inspection of the array transducer. FIG. 7A shows the waveform $V_T(t)$ of the driving signals, and FIGS. 7B and 7C show waveforms $V_R(t)$ of the detection signals of the ultrasonic transducers A and B, respectively.

Here, in the judgment whether the inspected ultrasonic transducer is a conforming product or not, the peak difference $(V_T)$pp of the top and bottom of the waveform of the driving signal and the peak difference $(V_R)$pp of the top and bottom of the waveform of the detection signal are compared, and it is judged as a conforming product if a ratio therebetween is larger than a predetermined value. For example, when L=15 mm, the ultrasonic transducer is judged as a conforming product if the following expression (1) is satisfied, and if not, it is judged as a defective product.

$$20 \cdot \log_{10}\{(V_R)pp/(V_T)pp\} > -60 dB \quad (1)$$

In the examples shown in FIGS. 7A to 7C, since the ultrasonic transducer A satisfies the expression (1), it is a conforming product, while, since the ultrasonic transducer B does not satisfy the expression (1), it is a defective product. In regard to the ultrasonic transducer that is judged as a conforming product, the waveform of the detection signal is converted into a frequency component by using Fast Fourier Transformation (FFT). Further, the peak difference $(V_R)$pp of the top and bottom of the waveform of the detection signal and a form of the spectrum of the detection signal are recorded.

Figure 8:
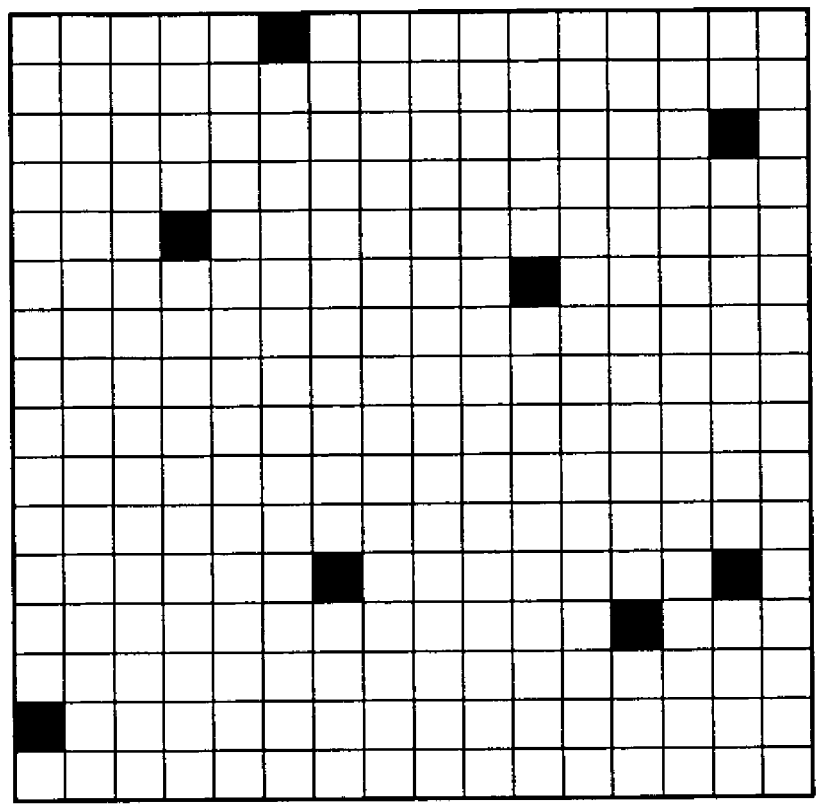
FIG. 8 is a diagram showing an array transducer having ultrasonic transducers that have been judged as defective products in the inspection of the array transducer.

As described above, as a result of inspecting all of the ultrasonic transducers included in the array transducer, the ultrasonic transducers that have been judged as defective products (hereinafter, also referred to "defective element") are shown in FIG. 8. In FIG. 8, black squares of the ultrasonic transducers arranged in a matrix form show positions of the defective elements.

In the embodiment, in the case where the defective elements are included at the positions in the arrangement patterns shown in FIGS. 3A and 3B in the inspected array transducer, the arrangement pattern of the ultrasonic transducers to be used is determined as follows while avoiding these defective elements.

Figure 9:
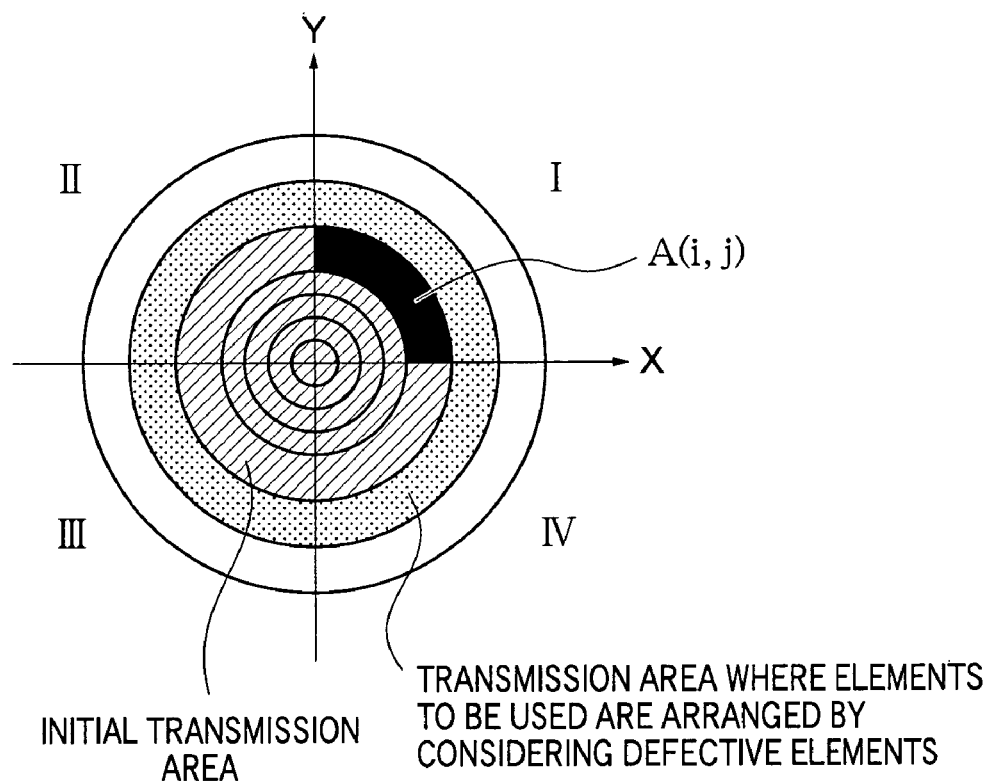
FIG. 9 is a schematic diagram showing a process of determining an arrangement pattern of the ultrasonic transducers for transmission while avoiding defective elements.
Figure 10:
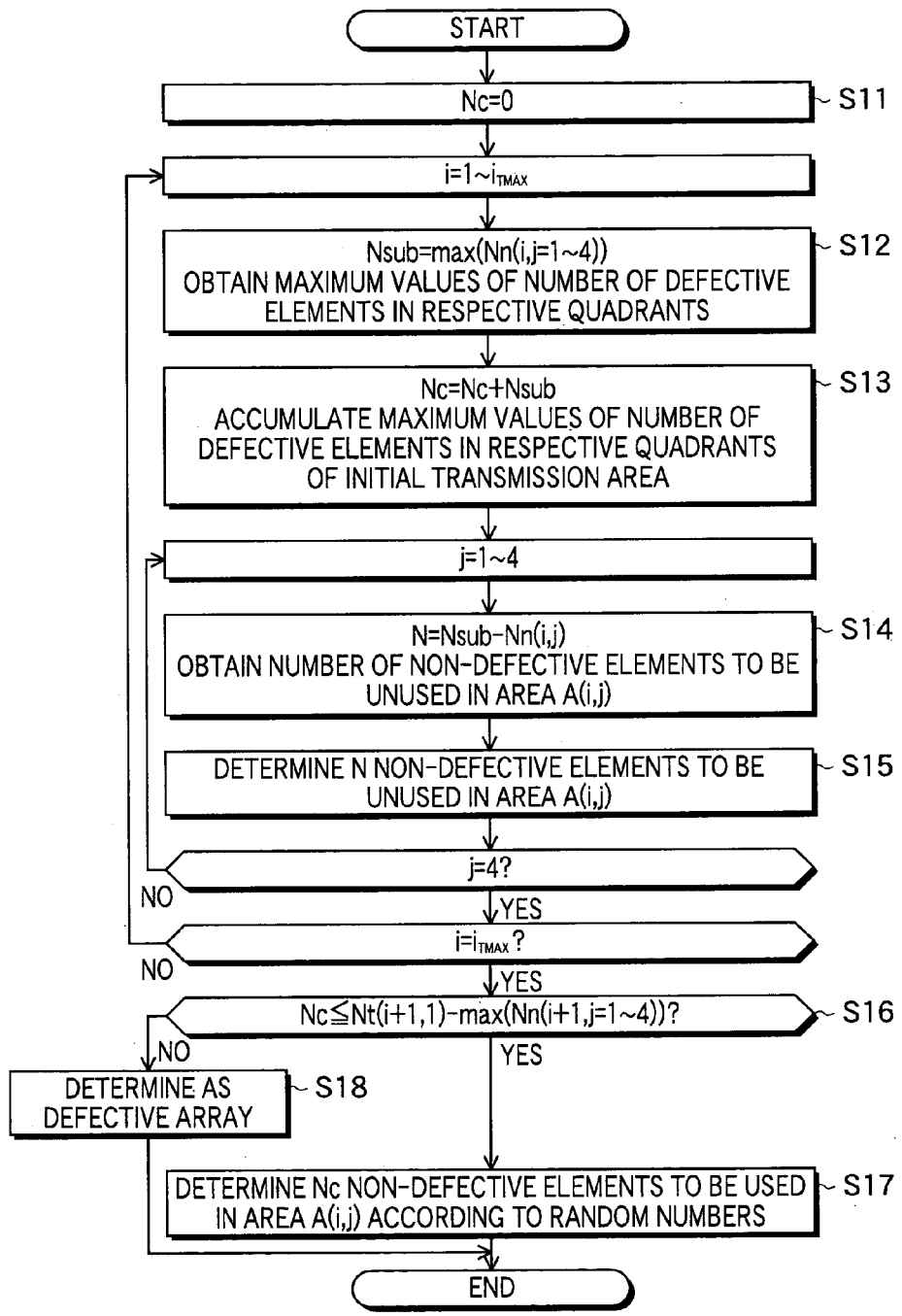
FIG. 10 is a flowchart showing an algorithm for determining the arrangement pattern of the ultrasonic transducers for transmission while avoiding defective elements.

FIG. 9 is a schematic diagram of the array transducer, in which a process of determining the arrangement pattern of the ultrasonic transducers for transmission while avoiding defective elements is shown, and FIG. 10 is a flowchart showing an algorithm for determining the arrangement pattern of the ultrasonic transducers for transmission while avoiding defective elements.

As shown in FIG. 9, in the case where the array transducer is divided by drawing plural concentric circles from the center of this array transducer, an area A(i, j) surrounded by the X axis and Y axis orthogonal to each other through the center of the array transducer is considered within a doughnut-shaped ring divided by two adjacent concentric circles. Here, i is a variable with regard to the radial direction, and j is a variable with regard to the respective quadrants (the first quadrant I to fourth quadrant IV) divided by the X and Y axes. That is, the area A(i, j) is an area located in the j-th quadrant within the i-th doughnut-shaped ring.

Here, it is assumed that the number of all of the ultrasonic transducers in the area A (i, j) is Nt(i, j), the number of the conforming products to be used in the area A (i, j) is Nu(i, j), and the number of the defective products in the area A (i, j) is Nn(i, j). Further, it is assumed that the number of the total rings in the array transducer is $I_{MAX}$, and the number of the rings to be used for transmission is $i_{TMAX}$, where $i_{TMAX} < I_{MAX}$. In the embodiment, a transmission area, in which elements to be used are arranged by considering the defective elements, is newly provided in the periphery of the initial transmission area shown in FIG. 3A.

Next, the algorithm shown in FIG. 10 for determining the arrangement pattern of the ultrasonic transducers for transmission while avoiding defective elements will be described.

First, at step S11, initialization is performed as Nc=0. Then, entering the first loop for varying the value of the variable i with regard to the radial direction in a range from 1 to $i_{TMAX}$. At step S12, the maximum values Nsub=max (Nn(i, j=1 to 4)) of the number of the defective elements in the first to fourth quadrants are obtained. At step 13, the value Nc is obtained by accumulating the maximum values Nsub of the number of the defective elements in the first to fourth quadrants of the initial transmission area (i=1 to $i_{TMAX}$) with regard to the radial direction.

Next, entering the second loop for varying the value of the variable j with regard to the respective quadrants in a range from 1 to 4. At step S14, the number of conforming products (non-defective elements) to be unused in the area A(i, j) is obtained as N=Nsub−Nn(i, j). Further, at step S15, the positions of the defective elements in the area A(i, j) are read in, and N non-defective elements to be unused in the area A(i, j) are determined according to random numbers. When the value of the variable j becomes 4, the process exits from the second loop. Further, when the value of the variable i becomes $i_{TMAX}$, the process exits from the first loop.

Next, at step 16, it is determined whether or not the value Nc that is obtained by accumulating the maximum values Nsub of the number of the defective elements in the first to fourth quadrants of the initial transmission area with regard to the radial direction is equal to or less than the value obtained by subtracting the number of the defective elements (the maximum value in the first to fourth quadrants) from the total number of the elements in the area A(i+1, 1) of one quadrant (for example, the first quadrant) adjacent to and outside of the initial transmission area (i.e., the minimum value of the number of the non-defective elements in the one quadrant adjacent to and outside of the initial transmission area). In the case where the cumulative value Nc of the number of the defective elements in the initial transmission area is equal to or less than the minimum value of the number of the non-defective elements in the area adjacent to and outside of the initial transmission area, the positions of the defective products in the area A(i+1,j) are read in, and Nc non-defective elements used in the area A (i+1, j) are determined according to random numbers at step S17. Subsequent to this step, the elements arranged in the first to fourth quadrants may be repositioned so as to be substantially the same in number. On the other hand, in the case where the cumulative value Nc of the defective elements in the initial transmission area is larger than the minimum value of the number of the non-defective elements in the area adjacent to and outside of the initial transmission area, this array transducer is judged as a defective product at step S18.

Figure 11:
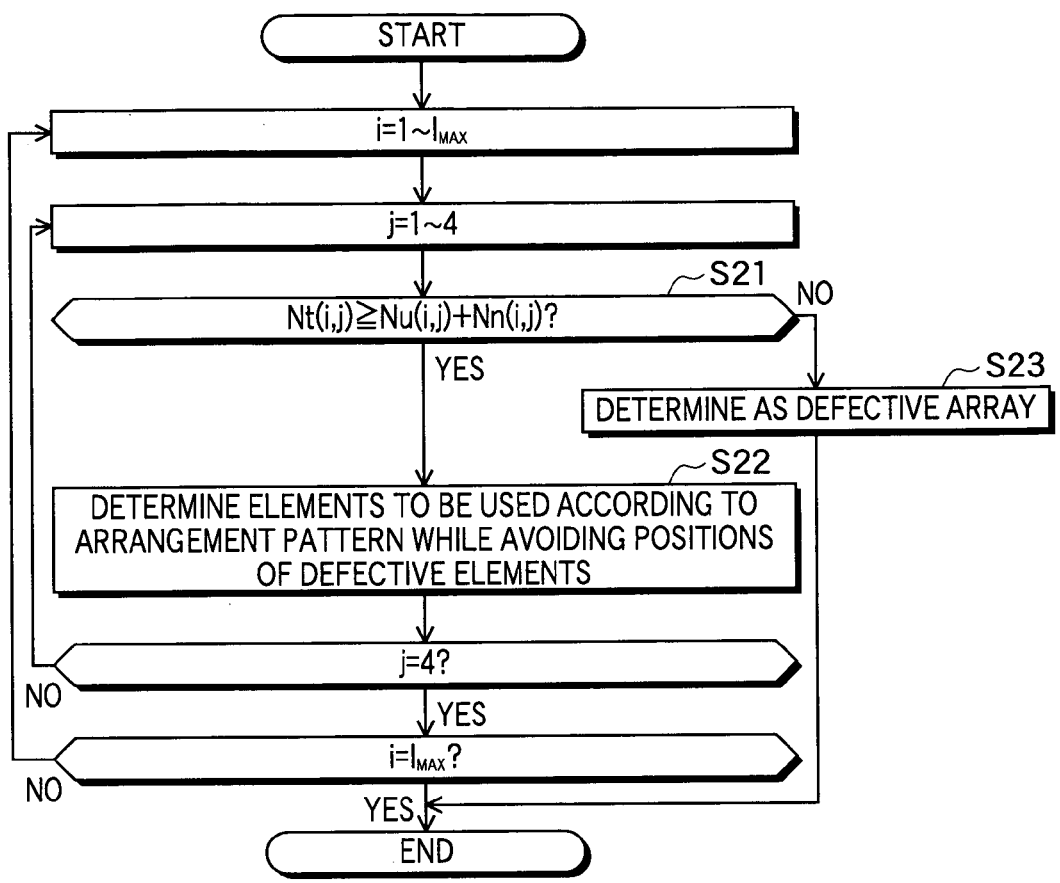
FIG. 11 is a flowchart showing an algorithm for determining an arrangement pattern of the ultrasonic transducers for reception while avoiding defective elements.

FIG. 11 is a flowchart showing an algorithm for determining the arrangement pattern of the ultrasonic transducers for reception while avoiding the defective elements.

First, the process enters the first loop for varying the value of the variable i with regard to the radial direction in a range from 1 to $i_{TMAX}$, and further, the process enters the second loop for varying the value of the variable j with regard to the respective quadrants in a range from 1 to 4. Then, at step S21, it is determined whether or not the total number Nt(i, j) of the ultrasonic transducers in the area A(i, j) is judged as being equal to or larger than the sum of the number Nu(i, j) of the non-defective elements to be used in the area A(i, j) and the number Nn(i, j) of the defective elements in the area A(i, j).

In the case where the total number Nt(i, j) of the ultrasonic transducers is equal to or more than the sum of the number Nu(i, j) of the non-defective elements and the number Nn(i, j) of the defective elements, at step 22, the positions of the defective elements in the area A(i, j) are read in, and the non-defective elements to be used in the area A(i, j) are determined according to the arrangement patterns as shown in FIGS. 3A to 3C. In the case where there are defective products in the positions corresponding to the arrangement pattern, elements in the vicinity thereof are selected. On the other hand, in the case where the total number Nt(i, j) of the ultrasonic transducers is less than the sum of the number Nu(i, j) of the non-defective elements and the number Nn (i, j) of the defective elements, at step S23, that array transducer is determined as a defective product and the process is ended. After the step S22, when the value of the variable j becomes 4, the process exits from the second loop, and when the value of the variable i becomes $i_{TMAX}$, the process exits from the first loop. Thereby, the ultrasonic transducers to be used for reception are arranged while avoiding defective ultrasonic transducers within the array transducer.

By using thus manufactured array transducer, an ultrasonic probe is fabricated. The used arrangement patterns of ultrasonic transducers are different between the manufactured plural ultrasonic probes, and the connecting relationships are also different between the ultrasonic transducers to be used and the electrodes of the connector used for connecting those ultrasonic transducers to the external apparatus main body. As a result, the delay amounts determined depending on the positional relationships between the positions of the respective ultrasonic transducers inside of the aperture of the array transducer and the object to be imaged become different between the manufactured plural ultrasonic probes. On this account, the ultrasonic transmitting and receiving apparatus main body 2 is adapted to identify the respective ultrasonic probes by attaching the identification information such as serial numbers to the respective ultrasonic probes. Alternatively, the ultrasonic transmitting and receiving apparatus main body 2 may be adapted to identify both models and serial numbers, etc. of the ultrasonic probes. The delay amounts relative to the ultrasonic transducers to be used in the respective ultrasonic probes are recorded in the recording unit 28 of the ultrasonic transmitting and receiving apparatus main body 2 in advance, or inputted to the ultrasonic transmitting and receiving apparatus main body 2 by using a recording medium such as a flexible disk or communicating means such as a network.

Further, by associating the probe identification information also with the characteristic information on the ultrasonic transducers, the ultrasonic transmitting and receiving apparatus main body 2 identifies the respective ultrasonic probes, thereby the characteristics of the transmission sensitivity or the reception sensitivity may be automatically adjusted in correspondence with the respective ultrasonic probes. This is for the following reasons.

In order to improve sensitivity and bandwidth of an ultrasonic probe, an ultrasonic probe using PZNT monocrystal is being developed. However, the ultrasonic probe using PZNT monocrystal has a defect that the variation of sensitivity (sensitivity irregularities) is larger than the conventional ultrasonic probe using PZT. In order to correct such sensitivity irregularities, the following methods are conceivable.

(1) A correction circuit is provided inside the ultrasonic probe to adjust each element independently.
(2) In the ultrasonic transmitting and receiving apparatus main body, the driving voltage is adjusted and the reception gain is adjusted.
(3) On the ultrasonic transmitting and receiving apparatus main body side, the numeric data after A/D conversion is corrected.

In the case where a two-dimensional array transducer is used, it is unrealistic that the sensitivity irregularities are adjusted for each element inside of the ultrasonic probe due to largeness of the number of the elements. On the other hand, in the case where the sensitivity irregularities are adjusted or corrected in the ultrasonic transmitting and receiving apparatus main body, it is necessary that the respective ultrasonic probes are identified on the ultrasonic transmitting and receiving apparatus main body side. In this case, the sensitivity irregularities can also be automatically adjusted or corrected because the ultrasonic transmitting and receiving apparatus main body identifies the respective ultrasonic probes by using the technique according to the embodiment. The characteristic information (sensitivity information, frequency characteristic information, etc.) of the ultrasonic transducers to be used in the respective ultrasonic probes is recorded in the recording unit 28 of the ultrasonic transmitting and receiving apparatus main body 2 (see FIG. 1) in advance, or inputted to the ultrasonic transmitting and receiving apparatus main body 2 by using a recording medium such as a flexible disk or communicating means such as a network.

In the ultrasonic transmitting and receiving apparatus main body 2, the control unit 27 may be adapted to adjust the transmission sensitivity by controlling the amplitude of the driving signal in each transmitting circuit 21, and further, to control the waveform of the driving signal by varying the frequency characteristics in each transmitting circuit 21. In addition, the control unit 27 may be adapted to adjust the reception sensitivity by controlling the gain in each receiving circuit 22, and further, to adjust the waveform and the SN ratio of the driving signal by controlling the bandwidth in each receiving circuit 22.

Figure 12:
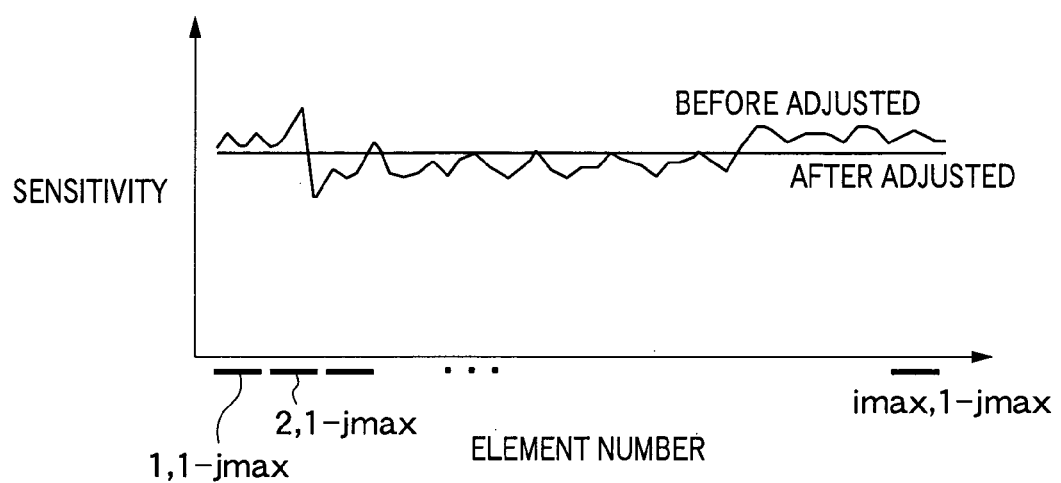
FIG. 12 is a diagram showing an example in which sensitivity irregularities are automatically adjusted in a two-dimensional array transducer.

FIG. 12 shows an example in which the sensitivity irregularities are automatically adjusted in the two-dimensional array transducer. In FIG. 12, the longitudinal axis indicates the element numbers of the ultrasonic transducers, and the lateral axis indicates the sensitivity of the ultrasonic transducers. The element numbers are given as from 1 to imax in the X axis direction of the two-dimensional array transducer, and as from 1 to jmax in the Y axis direction of the two-dimensional array transducer. FIG. 12 shows the sensitivity of the ultrasonic transducers in a specific column in the X axis direction. In the inspection, the sensitivity distribution (before adjusted) of these ultrasonic transducers can be obtained. By adjusting the voltage of the driving signal so that this sensitivity distribution may be constant in regard to all of the ultrasonic transducers, uniform sensitivity distribution (after adjusted) can be obtained. Further, by correcting the distribution with regard to the frequency characteristics of these ultrasonic transducers, uniform waveforms can be obtained.

Figure 13:
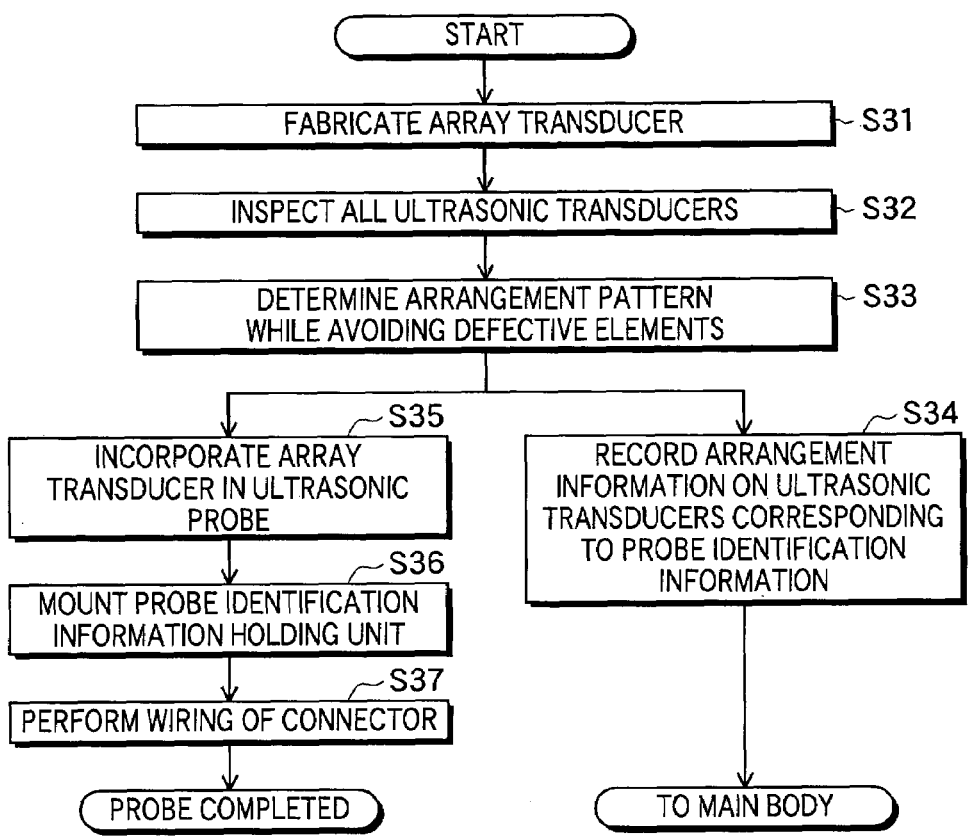
FIG. 13 is a flowchart showing a manufacturing method of the ultrasonic probe in one embodiment of the present invention.

Next, a manufacturing method of the ultrasonic probe according to one embodiment of the present invention will be described by referring to FIGS. 1 and 13. FIG. 13 is a flowchart showing the manufacturing method of the ultrasonic probe in one embodiment of the present invention.

First, at step S31, an array transducer 11 including plural ultrasonic transducers is fabricated. Then, at step S32, all of the ultrasonic transducers are inspected. At step S33, by arranging the ultrasonic transducers to be used while avoiding defective elements, the arrangement pattern of the ultrasonic transducers is determined. The arrangement information representing this arrangement pattern and/or the characteristic information on the ultrasonic transducers is recorded on a recording medium such as a flexible disk in correspondence with the probe identification information (step S34).

At step S35, the array transducer 11 is incorporated in the ultrasonic probe 1. At step S36, the probe identification information holding portion 12 is mounted to the ultrasonic probe 1. At step S37, wirings are provided between the ultrasonic transducers to be used and the primary side connector 3, and wirings are provided between the probe identification information holding portion 12 and the primary side connector 3. Thereby, the ultrasonic probe 1 is completed. In the case where identification of the ultrasonic probe is not performed in the ultrasonic transmitting and receiving apparatus main body, steps S33, S34, and S35 can be omitted.

Figure 14:
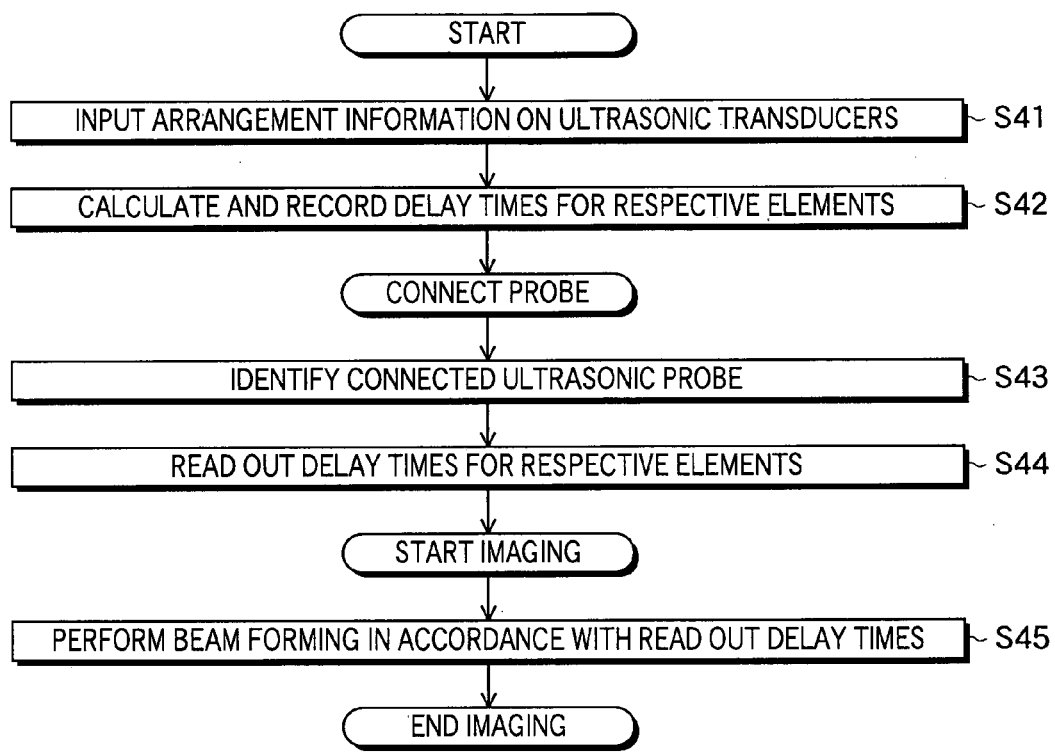
FIG. 14 is a flowchart showing operation of the ultrasonic transmitting and receiving apparatus according to one embodiment of the present invention.

Next, operation of the ultrasonic transmitting and receiving apparatus according to one embodiment of the present invention will be described by referring to FIGS. 1 and 14. FIG. 14 is a flowchart showing the operation of the ultrasonic transmitting and receiving apparatus according to one embodiment of the present invention.

At step S41, by using the recording medium such as a flexible disk on which the arrangement information and/or characteristic information has been recorded at the step S34 in FIG. 13 or via a network, etc., the arrangement information representing the arrangement pattern of the ultrasonic transducers and/or characteristic information representing characteristics of the ultrasonic transducers is inputted to the ultrasonic transmitting and receiving apparatus main body 2 in correspondence with the probe identification information.

At step S42, the control unit 27 calculates the delay amounts for the respective elements on the basis of this arrangement information, etc., and controls the recording unit 28 to record the delay amount table corresponding to the probe identification information. Thereby, delay amount information inherent in the ultrasonic probes is taken in the ultrasonic transmitting and receiving apparatus main body 2. By the way, the delay amounts maybe obtained in the external apparatus and supplied the delay amount table to the ultrasonic transmitting and receiving apparatus main body 2 as a data file. Alternatively, the arrangement information, etc. representing the arrangement pattern of the ultrasonic transducers may be recorded in the recording unit 28 without being processed, and when performing imaging, the delay amounts for the respective elements may be calculated in the control unit 27. Further, in the case where the characteristic information representing the characteristics of the ultrasonic transducers is inputted in the ultrasonic transmitting and receiving apparatus main body 2, the control unit 27 controls the recording unit 28 to record this.

When the ultrasonic probe 1 is connected to the ultrasonic transmitting and receiving apparatus main body 2, the control unit 27 recognizes the probe identification information on the basis of the status of the probe identification electrodes 33 of the secondary side connector 3b, and identifies the connected ultrasonic probe 1 (step S43). At step S44, the control unit 27 reads out the delay amount table corresponding to the probe identification information (serial numbers, etc.) from the recording unit 28. Further, in the case where the characteristic information representing the ultrasonic transducers is recorded in the recording unit 28, the control unit 27 reads this out from the recording unit 28.

When the ultrasonic imaging is started, the control unit 27 performs transmission beam forming by controlling the delay amounts of the plural driving signals in the plural transmitting circuits 21 in accordance with the delay amount table that has been read out from the recording unit 28, and performs reception beam forming by controlling the delay amounts of the plural detection signals in the plural transmitting circuits 22 (step S45). Here, the control unit 27 can adjust the transmission sensitivity, reception sensitivity, etc. on the basis of the characteristic information read out from the recording nit 28.

As described above, according to the present invention, by selecting ultrasonic transducers to be used while avoiding the ultrasonic transducers out of the specifications, the arrangement of the ultrasonic transducers to be used in one array transducer is determined. Further, the arrangement information and/or the characteristic information on the used ultrasonic transducers has been recorded by being associated with the identification information on that ultrasonic probe, and utilized in the ultrasonic transmitting and receiving apparatus main body. Therefore, the array transducer, which has been unable to be used because it includes the ultrasonic transducers out of the specifications, can be used so that the yield in the manufacture of array transducers is improved.

What is claimed is:

1. An ultrasonic probe to be used when connected to an external apparatus main body, said probe comprising:
    a transducer array having a first number of ultrasonic transducers arranged in a two-dimensional matrix form, said first number of ultrasonic transducers including ultrasonic transducers in an original pattern that are previously determined to be working and ultrasonic transducers outside of said original pattern;
    connecting means for connecting a second number of ultrasonic transducers selected from among said first number of ultrasonic transducers to said external apparatus main body, said second number being less than said first number and said second number of ultrasonic transducers including (i) ultrasonic transducers in said original pattern except for at least one defective ultrasonic transducer and (ii) at least one additional ultrasonic transducer outside of said original pattern in place of said at least one defective ultrasonic transducer; and identification information holding means for holding identification information on said ultrasonic probe, said identification information being associated with arrangement information and/or characteristic information on said selected second number of ultrasonic transducers within said transducer array.

2. An ultrasonic probe according to claim 1, wherein said connecting means includes wiring and electrodes for supplying the identification information on said ultrasonic probe held
by said identification information holding means to said external apparatus main body.

3. An ultrasonic probe to be used when connected to an external apparatus main body, said probe comprising:
a transducer array having a first number of ultrasonic transducers arranged in a two-dimensional matrix form, said first number of ultrasonic transducers including ultrasonic transducers in an original pattern that are previously determined to be working and ultrasonic transducers outside of said original pattern; and
a connector, having plural electrodes, for connecting a second number of ultrasonic transducers selected from among said first number of ultrasonic transducers to said external apparatus main body, said second number being less than said first number and said second number of ultrasonic transducers including (i) ultrasonic transducers in said original pattern except for at least one defective ultrasonic transducer and (ii) at least one additional ultrasonic transducer outside of said original pattern in place of said at least one defective ultrasonic transducer, wherein at least two kinds of connecting relationships between said selected ultrasonic transducers and said plural electrodes are set up in regard to plural ultrasonic probes.

4. An ultrasonic transmitting and receiving apparatus to be used when connected to an ultrasonic probe including a transducer array having a first number of ultrasonic transducers arranged in a two-dimensional matrix form, said first number of ultrasonic transducers including ultrasonic transducers in an original pattern that are previously determined to be working and ultrasonic transducers outside of said original pattern connecting means for connecting a second number of ultrasonic transducers selected from among said first number of ultrasonic transducers to an ultrasonic transmitting and receiving apparatus main body, said second number being less than said first number and said second number of ultrasonic transducers including (i) ultrasonic transducers in said original pattern except for at least one defective ultrasonic transducer and (ii) at least one additional ultrasonic transducer outside of said original pattern in place of said at least one defective ultrasonic transducer, and identification information holding means for holding identification information, said apparatus comprising:
plural transmitting circuits for respectively generating plural driving signals to be supplied to said ultrasonic probe so as to transmit an ultrasonic beam;
plural receiving circuits for respectively processing plural detection signals outputted from said ultrasonic probe which has received an ultrasonic echo; and
control means for controlling delay amounts of the plural driving signals in said plural transmitting circuits and/or delay amounts of the plural detection signals in said plural receiving circuits in correspondence with the ultrasonic probe identified on the basis of the identification information such that said at least one additional ultrasonic transducer works in place of said at least one defective ultrasonic transducer.

5. An ultrasonic transmitting and receiving apparatus according to claim 4, wherein said control means calculates delay amounts on the basis of arrangement information and/or characteristic information on said selected second number of ultrasonic transducers with regard to plural ultrasonic probes in advance, and controls recording means to record delay amount tables in correspondence with the identification information on the respective ultrasonic probes.

6. An ultrasonic transmitting and receiving apparatus according to claim 5, wherein said control means controls said recording means to read out a delay amount table corresponding to the identification information supplied by said connecting means.

7. An ultrasonic transmitting and receiving apparatus to be used when connected to an ultrasonic probe including a transducer array having a first number of ultrasonic transducers arranged in a two-dimensional matrix form, said first number of ultrasonic transducers including ultrasonic transducers in an original pattern that are previously determined to be working and ultrasonic transducers outside of said original pattern, connecting means for connecting a second number of ultrasonic transducers selected from among said first number of ultrasonic transducers to an ultrasonic transmitting and receiving apparatus main body, said second number being less than said first number and said second number of ultrasonic transducers including (i) ultrasonic transducers in said original pattern except for at least one defective ultrasonic transducer and (ii) at least one additional ultrasonic transducer outside of said original pattern in place of said at least one defective ultrasonic transducer, and identification information holding means for holding identification information, said apparatus comprising:
plural transmitting circuits for respectively generating plural driving signals to be supplied to said ultrasonic probe so as to transmit an ultrasonic beam;
plural receiving circuits for respectively processing plural detection signals outputted from said ultrasonic probe which has received an ultrasonic echo; and
control means for controlling amplitudes and/or waveforms of the plural driving signals in said plural transmitting circuits in correspondence with the ultrasonic probe identified on the basis of the identification information such that said at least one additional ultrasonic transducer works in place of said at least one defective ultrasonic transducer.

8. An ultrasonic transmitting and receiving apparatus to be used when connected to an ultrasonic probe including a transducer array having a first number of ultrasonic transducers arranged in a two-dimensional matrix form, said first number of ultrasonic transducers including ultrasonic transducers in an original pattern that are previously determined to be working and ultrasonic transducers outside of said original pattern, connecting means for connecting a second number of ultrasonic transducers selected from among said first number of ultrasonic transducers to an ultrasonic transmitting and receiving apparatus main body, said second number being less than said first number and said second number of ultrasonic transducers including (i) ultrasonic transducers in said original pattern except for at least one defective ultrasonic transducer and (ii) at least one additional ultrasonic transducer outside of said original pattern in place of said at least one defective ultrasonic transducer, and identification information holding means for holding identification information, said apparatus comprising:

plural transmitting circuits for respectively generating plural driving signals to be supplied to said ultrasonic probe so as to transmit an ultrasonic beam;

plural receiving circuits for respectively processing plural detection signals outputted from said ultrasonic probe which has received an ultrasonic echo; and control means for controlling gains and/or bandwidths in said plural receiving circuits in correspondence with the ultrasonic probe identified on the basis of the identification information such that said at least one additional ultrasonic transducer works in place of said at least one defective ultrasonic transducer.

\* \* \* \* \*